US011607454B2

United States Patent
Wilson et al.

(10) Patent No.: US 11,607,454 B2
(45) Date of Patent: Mar. 21, 2023

(54) DEVICES AND PROCESSES FOR CHERENKOV-ACTIVATED NUCLEAR-TARGETED PHOTODYNAMIC THERAPY

(71) Applicants: UNIVERSITY HEALTH NETWORK, Toronto (CA); THE GOVERNING COUNCIL OF THE UNIVERSITY OF TORONTO, Toronto (CA)

(72) Inventors: Brian Wilson, Toronto (CA); Christine Allen, Toronto (CA)

(73) Assignee: UNIVERSITY HEALTH NETWORK, Toronto (CA)

(*) Notice: Subject to any disclaimer, the term of this patent is extended or adjusted under 35 U.S.C. 154(b) by 676 days.

(21) Appl. No.: 16/303,400

(22) PCT Filed: May 19, 2017

(86) PCT No.: PCT/CA2017/050614
§ 371 (c)(1),
(2) Date: Nov. 20, 2018

(87) PCT Pub. No.: WO2017/197531
PCT Pub. Date: Nov. 23, 2017

(65) Prior Publication Data
US 2020/0316200 A1 Oct. 8, 2020

Related U.S. Application Data

(60) Provisional application No. 62/339,165, filed on May 20, 2016.

(51) Int. Cl.
A61K 41/00 (2020.01)
A61N 5/10 (2006.01)

(52) U.S. Cl.
CPC ...... *A61K 41/0038* (2013.01); *A61K 41/0071* (2013.01); *A61N 5/10* (2013.01); *A61N 2005/1098* (2013.01)

(58) Field of Classification Search
CPC .............. A61K 47/6907; A61K 47/62; A61K 47/6935; A61K 41/0038; A61K 41/0071;
(Continued)

(56) References Cited

U.S. PATENT DOCUMENTS 6,500,800 B1 * 12/2002 Sobolev ................. A61K 47/65
514/1.2
2003/0083649 A1 * 5/2003 Margaron .......... A61K 41/0071
606/4
(Continued)

FOREIGN PATENT DOCUMENTS

WO 2015183346 A2 12/2015
WO 2017075057 A1 5/2017

OTHER PUBLICATIONS

WIPO, International Search Report and Written Opinion for International Application No. PCT/CA2017/050614 dated Aug. 24, 2017.
(Continued)

*Primary Examiner* — Christine H Matthews
*Assistant Examiner* — Joshua Daryl D Lannu
(74) *Attorney, Agent, or Firm* — Norton Rose Fulbright Canada LLP (57) ABSTRACT

Devices, materials, compounds, systems, and processes for Cherenkov-Activated Nuclear-Targeted Photodynamic Therapy that involves generating Cherenkov light within the tissue of a target volume and using this light to activate photosensitizing material that is located in the nucleus of cells of the target volume.

22 Claims, 10 Drawing Sheets (58) Field of Classification Search
CPC .......... A61K 47/593; A61N 2005/1098; A61N 2005/0626; A61N 5/10; A61N 5/062; C12N 15/01
See application file for complete search history.

(56) References Cited

U.S. PATENT DOCUMENTS

2007/0218049 A1* 9/2007 Chen ..................... A61K 33/00
424/130.1
2018/0311355 A1* 11/2018 Oldham ............... A61K 33/242

OTHER PUBLICATIONS

Extended European Search Report dated Jan. 8, 2020 in EP 17798468.9.
Kascakova, Slavka et al., X-ray-induced radiophotodynamic therapy (RPDT) using lanthanide micelles: Beyond depth limitations, Nano Research, Tsinghua University Press, CN, vol. 8, No. 7, May 20, 2015, pp. 2373-2379, XP035514582, ISSN: 1998-0124.
Fan, Wenpei et al., Intranuclear biophotonics by smart design of nuclear-targeting photo-/radio-sensitizers co-loaded upconversion nanoparticles, Biomaterials, Elsevier Science Publishers BV., Barking, GB, vol. 69, Aug. 8, 2015, pp. 89-98, XP029262052, ISSN: 0142-9612.
Scaffidi, Jonathan P. et al., Activity of Psoralen-Functionalized Nanoscintillators against Cancer Cells upon X-ray Excitation, ACS Nano, vol. 5, No. 6, Jun. 28, 2011, pp. 4679-4687, XP055406306.

* cited by examiner

DEVICES AND PROCESSES FOR
CHERENKOV-ACTIVATED
NUCLEAR-TARGETED PHOTODYNAMIC
THERAPY

FIELD

The present disclosure generally relates to the field of photodynamic therapy (PDT) treatment.

INTRODUCTION

Photodynamic therapy (PDT) may use visible or near-infrared light to activate minimally-toxic compounds or photosensitizers as an approved modality for a range of solid tumors and pre-malignant lesions, as well as a several non-oncologic conditions such as age-related macular degeneration and localized infections, and benign dermatological conditions. However, its adoption into clinical oncology has been slow despite its several significant advantages that include minimal off-target toxicity, excellent tissue healing, repeatability, no induced resistance, compatibility with other modalities, relatively low cost, and triggering of anti-tumor immunity.

Photodynamic photosensitizers can be targeted to the cell nucleus in order to reduce the dose of photosensitizer required to achieve a given cell death upon photodynamic activation with light. For example, for cells in vitro, nuclear localization can reduce the required dose of the photosensitizer chlorine 6 by greater than 100-fold by conjugation to branched peptides (loligomers) with nuclear-targeting sequences.

There may be an enhanced effect when adenoviruses were used in combination with nuclear localizing signals to enhance the PDT cytotoxicity of the same photosensitizer. There can be increased PDT efficacy by nuclear targeting utilizing nanoparticles. In all cases reported, the photodynamic action was initiated by the use of visible or near-infrared light generated by an external source such as a laser. This type of photoactivation is common in photodynamic therapy, independent of the type or intracellular localization of the photosensitizer, but is not practical for many clinical applications in oncology.

The use of Cherenkov radiation generated by X-rays or Gamma-rays to serve as the light source for PDT has been investigated in a number of studies, both theoretically and experimentally in cells in vitro and in model tumors in vivo. For example, a radioactive material (copper-84 or fluorine-18) can be used to locally generate Cherenkov light from the radioactive emissions of a beta-particle together with titanium dioxide nanoparticles that are activated by ultraviolet radiation. This may involve direct intratumoral injection of large doses of both radionuclide and photosensitizer.

The use of linac-generated Cherenkov light together with systemic administration of nuclear targeted photosensitizer might be able to reach large and deep-seated tumors. However, it is not clear that the intensity of linac-generated Cherenkov light is high enough to give an effective PDT response at an X-ray dose that is not itself substantively therapeutic or, in the alternative, that an X-ray dose corresponding to high-intensity linac-generated Cherenkov light might not carry significant risk of damage to normal tissues. Radiation therapy treatments can be around 50 Gy given in multiple smaller-dose fractions, so that single X-ray doses used for Cherenkov light activation may be less than 10 Gy.

There may be conditions of adequate Cherenkov light so that clinically-achievable photosensitizer doses can be met. An order-of-magnitude reduction in the required PDT light dose can be achieved using an external light source generating short-wavelength light for which the photosensitizer absorption is very strong. However, the penetration of this light through tissues can be poor so that this might not provide a clinically realistic approach for other than superficial disease. Cherenkov light generation and propagation in tissue can be modeled. PDT may remain clinically impractical at the low light fluence values associated with Cherenkov light in tissue.

SUMMARY

In accordance with an aspect, embodiments described herein can circumvent the limitation of low intensity (fluence rate) of X-ray generated Cherenkov light by exploiting the large increase in the photodynamic cell kill that can be achieved by having the photosensitizer targeted to the cell nucleus rather than being localized in cytoplasmic organelles such as mitochondria that are the primary targets for photodynamic damage and cell kill in conventional PDT as currently practiced with external light sources such as lasers, light emitting diodes or filtered lamps. There may be an option of using external X-ray sources as the Cherenkov light source for photodynamic therapy.

In accordance with an aspect, there is provided a device for photodynamic therapy configured to generate Cherenkov light by ionizing radiation to activate photosensitizing material located within the nucleus of cells of a target volume. Cherenkov light is understood to be encompassed within the secondary products of ionizing radiation in tissue that also include secondary electrons. Both Cherenkov light and secondary electrons are understood to have the capability to activate photosensitizing materials.

In accordance with an aspect, there is provided a process for photodynamic therapy comprising generating Cherenkov light by ionizing radiation and activating photosensitizing material located within the nucleus of cells of a target volume.

In accordance with an aspect, there is provided a process for generating Cherenkov light in which the high sensitivity of the cell nucleus to damage from the photoproducts generated within the nucleus compensates for the low radiant energy density of the Cherenkov light produced using doses of ionizing radiation that are substantially below the dose required to kill or substantially damage the cells.

In accordance with an aspect, there is provided a process for photodynamic therapy comprising activating photosensitizing material located within a nucleus of cells by generating Cherenkov light within the tissue by ionizing radiation.

In accordance with an aspect, there is provided a process for photodynamic therapy comprising locating photosensitizing material within the nucleus of cells, generating Cherenkov light and ionizing radiation to activate the photosensitizing material located within the nucleus of cells.

In accordance with an aspect, there is provided a process for photodynamic therapy comprising targeting photosensitizing material to nucleus of cells and generating Cherenkov light source within the tissue or nucleus of cells.

In accordance with an aspect, there is provided a process in which the Cherenkov light is generated within tissue.

In accordance with an aspect, there is provided a process in which the Cherenkov light is generated in dielectric material in close proximity to the tissue.

In accordance with an aspect, there is provided a process in which the cells of the target volume are tumor cells.

In accordance with an aspect, there is provided a process in which the cells of the target volume are other diseased cells, such as cancer cells or vascular endothelial cells in tumors.

In accordance with an aspect, there is provided a process in which the cells are killed or modified by the photoproducts generated by the activation of the photosensitizing material.

In accordance with an aspect, there is provided a process in which the ionizing radiation comprises a beam of X-rays of energy around 1 MeV or higher.

In accordance with an aspect, there is provided a process in which the ionizing radiation comprises a beam of electrons or other electrically charged particles of energy around 1 MeV or higher.

In accordance with an aspect, there is provided a process in which the ionizing radiation comprises charged particles from radioactive decay.

In accordance with an aspect, the biocompatible materials comprise nanoparticles formed from amphiphilic block copolymers that entrap the photosensitizing material and deliver it to the nucleus of cells.

In accordance with an aspect, the biocompatible materials are conjugated with TAT peptide for nuclear entry.

In accordance with another aspect, there is provided nanoparticles comprising amphiphilic block copolymers with diameters of 10-100 nm that chemically and physically entrap photosensitizes and include targeting moieties at the surface of the particles to ensure cellular entry and nuclear localization.

In accordance with another aspect, there is provided a polymeric nanotechnology formed from amphiphilic copolymer that include a hydrophilic poly(ethylene glycol block) and a hydrophobic poly(ester) or poly(amino acid) block or polymer with similar properties.

In accordance with another aspect, there is provided a device for activating photosensitizing material located within a nucleus of cells by generating Cherenkov light by ionizing radiation.

In accordance with another aspect, there is provided a system comprising nuclear-targeted PDT agent(s), Cherenkov light source, a treatment planning unit and radiation-optical dosimetry instruments to individually optimize treatments.

In various further aspects, the disclosure may provide corresponding processes, systems, compounds and devices, and logic structures such as machine-executable coded instruction sets for implementing such systems, devices, and methods.

In accordance with another aspect, there is provided a method of causing nuclear DNA damage that can involve: delivering photosensitizing material to a nucleus of tissue cells, wherein the photosensitizing material is targeted to the nucleus of the tissue cells using a nucleus delivery agent; activating the photosensitizing material by exposing it to secondary products of ionizing radiation generated when the ionizing radiation is directed at tissue; and causing DNA damage in the tissue cells by photoproducts generated by activation of the photosensitizing material.

In some embodiments, the secondary products of ionizing radiation can include Cherenkov light.

In some embodiments, the photosensitizing material is a porphyrin.

In some embodiments, the porphyrin is tetraphenylporphyrin.

In some embodiments, the nucleus delivery agent can include a nuclear localizing signal attached to the photosensitizing material.

In some embodiments, the nucleus delivery agent can include a nuclear localizing signal attached to a nanosized carrier that incorporates the photosensitizing material.

In some embodiments, the nanosized carrier is formed from polymers, lipids or small-molecule surfactants.

In some embodiments, the nanosized carrier is a block-copolymer micelle.

In accordance with another aspect, there is provided a method of photodynamic therapy that can involve: delivering photosensitizing material to the nucleus of tissue cells, wherein the photosensitizing material is targeted to the nucleus of the tissue cells using a nucleus delivery agent; activating the photosensitizing material by exposing it to secondary products of ionizing radiation generated when the ionizing radiation is directed at tissue, the ionizing radiation being at a dosage level that in the absence of the photosensitizing agent is not therapeutically effective; and causing DNA damage in the tissue cells by photoproducts generated by activation of the photosensitizing material.

In some embodiments, the secondary products of ionizing radiation can include Cherenkov light.

In some embodiments, the photosensitizing material is a porphyrin.

In some embodiments, the porphyrin is tetraphenylporphyrin.

In some embodiments, the nucleus delivery agent can include a nuclear localizing signal attached to the photosensitizing material.

In some embodiments, the nucleus delivery agent can include a nuclear localizing signal attached to a nanosized carrier that incorporates the photosensitizing material.

In some embodiments, the nanosized carrier is formed from polymers, lipids or small-molecule surfactants.

In some embodiments, the nanosized carrier is a block-copolymer micelle.

In accordance with another aspect, there is provided a method of increasing the effectiveness of ionizing radiation treatment that involves: delivering photosensitizing material to the nucleus of tissue cells, wherein the photosensitizing material is targeted to the nucleus of the tissue cells using a nucleus delivery agent; activating the photosensitizing material by exposing it to secondary products of ionizing radiation generated when the ionizing radiation is directed at tissue; and causing DNA damage in the tissue cells by photoproducts generated by activation of the photosensitizing material, wherein the DNA damage caused is in addition to the DNA damage caused by ionizing radiation alone.

In some embodiments, the secondary products of ionizing radiation can include Cherenkov light.

In some embodiments, the photosensitizing material is a porphyrin.

In some embodiments, the porphyrin is tetraphenylporphyrin.

In some embodiments, the nucleus delivery agent includes a nuclear localizing signal attached to the photosensitizing material.

In some embodiments, the nucleus delivery agent comprises a nuclear localizing signal attached to a nanosized carrier that incorporates the photosensitizing material.

In some embodiments, the nanosized carrier is formed from polymers, lipids or small-molecule surfactants.

In some embodiments, the nanosized carrier is a block-copolymer micelle.

In accordance with another aspect, there is provided a device for photodynamic therapy configured to deliver photosensitizing material to the nucleus of tissue cells, wherein the photosensitizing material is targeted to the nucleus of the tissue cells using a nucleus delivery agent; and activate the photosensitizing material by exposing it to secondary products of ionizing radiation generated when the ionizing radiation is directed at tissue, wherein DNA damage is caused in the tissue cells by photoproducts generated by activation of the photosensitizing material.

In some embodiments, the secondary products of ionizing radiation comprise Cherenkov light.

In some embodiments, the photosensitizing material is a porphyrin.

In some embodiments, the porphyrin is tetraphenylporphyrin.

In some embodiments, the nucleus delivery agent comprises a nuclear localizing signal attached to the photosensitizing material.

In some embodiments, the nucleus delivery agent comprises a nuclear localizing signal attached to a nanosized carrier that incorporates the photosensitizing material.

In some embodiments, the nanosized carrier is formed from polymers, lipids or small-molecule surfactants.

In some embodiments, the nanosized carrier is a block-copolymer micelle.

In some embodiments, the ionizing radiation is at a dosage level that in the absence of the photosensitizing agent is not therapeutically effective.

In accordance with another aspect, there is provided a method of photodynamic therapy that involves: delivering photosensitizing material to the nuclei of tissue cells, wherein the photosensitizing agent is targeted to the nucleus of such cells using a nucleus delivery agent; and activating the photosensitizing material by exposing the tissue cells to Cherenkov light generated by ionizing radiation, the ionizing radiation at a dosage level that in the absence of the photosensitizing agent is not therapeutically active.

In some embodiments, the photosensitizing agent activated by the Cherenkov light damages the nuclear DNA of the tissue cells.

In accordance with another aspect, there is provided a device for photodynamic therapy configured to: deliver photosensitizing material to the nuclei of tissue cells, wherein the photosensitizing agent is targeted to the nucleus of such cells using a nucleus delivery agent; and activate the photosensitizing material by exposing the tissue cells to Cherenkov light generated by ionizing radiation, the ionizing radiation at a dosage level that in the absence of the photosensitizing agent is not therapeutically active.

In some embodiments, the photosensitizing agent activated by the Cherenkov light damages the nuclear DNA of the tissue cells.

In this respect, before explaining at least one embodiment in detail, it is to be understood that the embodiments are not limited in application to the details of construction and to the arrangements of the components set forth in the following description or illustrated in the drawings. Also, it is to be understood that the phraseology and terminology employed herein are for the purpose of description and should not be regarded as limiting.

There may be further features and combinations concerning embodiments described herein.

DESCRIPTION OF THE FIGURES

In the figures, embodiments are illustrated by way of example. It is to be expressly understood that the description and figures are only for the purpose of illustration and as an aid to understanding.

Embodiments will now be described, by way of example only, with reference to the attached figures, wherein in the figures.

DETAILED DESCRIPTION

Photosensitizing material may be activated by light from light sources. Example light sources include lasers, light-emitting diodes or spectrally-filtered lamps or other devices. However, it may be difficult to adequately deliver and distribute the light to treat large target volumes (e.g. large tumors) and deep-seated target volumes (e.g. deep-seated tumors). In the former it may be difficult to achieve good light dose uniformity throughout the target tissue volume. In both the former and the latter the light may be delivered via optical fibers, for example, either through an endoscope or interstitially through needles placed into the tissue. These procedures require additional technologies and skilled operators, particularly in the case where there is curative intent requiring complete tumor coverage by the light. Partly as a result of these technical requirements, PDT may not be used as first-line therapy for most tumors and may not be suitable for many tumors where the light cannot be delivered adequately to ensure complete light activation of the photosensitizer throughout the tumor volume.

Embodiments described herein may provide devices, processes, compounds and materials for Cherenkov-Light (CL) based photodynamic therapy (PDT). Embodiments described herein may use CL as the light source for PDT of a target volume, where tumors may be an example treatment application. Other potential clinical applications may be for both oncologic and non-oncologic diseases. Embodiments described herein enable PDT to be used, including for treatment of larger tumors and tumors that are located deep within the body without the requirement to deliver activating light throughout the tumor from remote light sources such as lasers or light emitting diodes or lamps.

Figure 1:
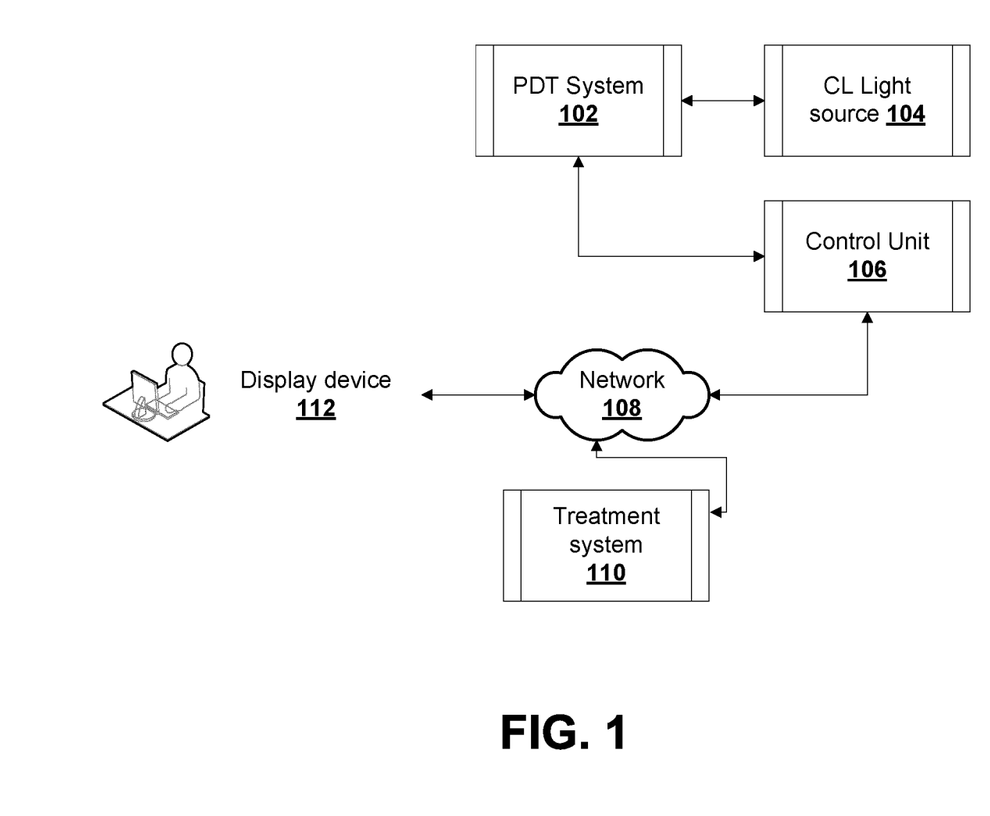
FIG. 1 is a view of an example system for photodynamic therapy according to some embodiments.

FIG. 1 is a view of an example system for CL based PDT with an improved CL light source while retaining some of the advantages of PDT. The example system includes a PDT system 102 that is configured to generate CL light source 104 by ionizing radiation according to some embodiments described herein. The CL light source 104 may be generated by the passage of high-energy charged particles through tissue, for example as produced by high energy X-rays in the MeV range directed into the tissue.

The PDT system 102 provides nuclear targeting of photosensitizing material. The PDT system 102 may include PDT agents, compounds or photosensitizers (PS) (collectively referred to as photosensitizing material) provided as a PDT photoactive material. For example, the photosensitizing material may include biocompatible materials that conjugate with Trans-Activator of Transcription (TAT) peptide for nuclear entry. The photosensitizing material in cell nucleus is activated by the CL light source 104.

The PDT system 102 may include radiation-optical dosimetry instruments and may include an apparatus for generating ionizing radiation such as external-ray beams, high energy electrons or other charged particles or radionuclides. For example, PDT system 102 may involve ionizing radiation with a beam of X-rays of energy around 1 MeV or higher. As another example, PDT system 102 may involve ionizing radiation with a beam of electrons or other electrically charged particles of energy around 1 MeV or higher as components of PDT system 102. As a further example, PDT system 102 may involve ionizing radiation with charged particles from radioactive decay.

PDT system 102 may include a mechanism for contacting cells of a target volume with the photosensitizing material so that the photosensitizing material may be located within the nucleus of cells. In some example embodiments, the photosensitizing material can be applied locally to the target volume. In some example embodiments, the photosensitizing material can be administered regionally or systemically and will subsequently localize to the target volume. In some example embodiments, photosensitive targets can be locally activated by light.

Figure 3:
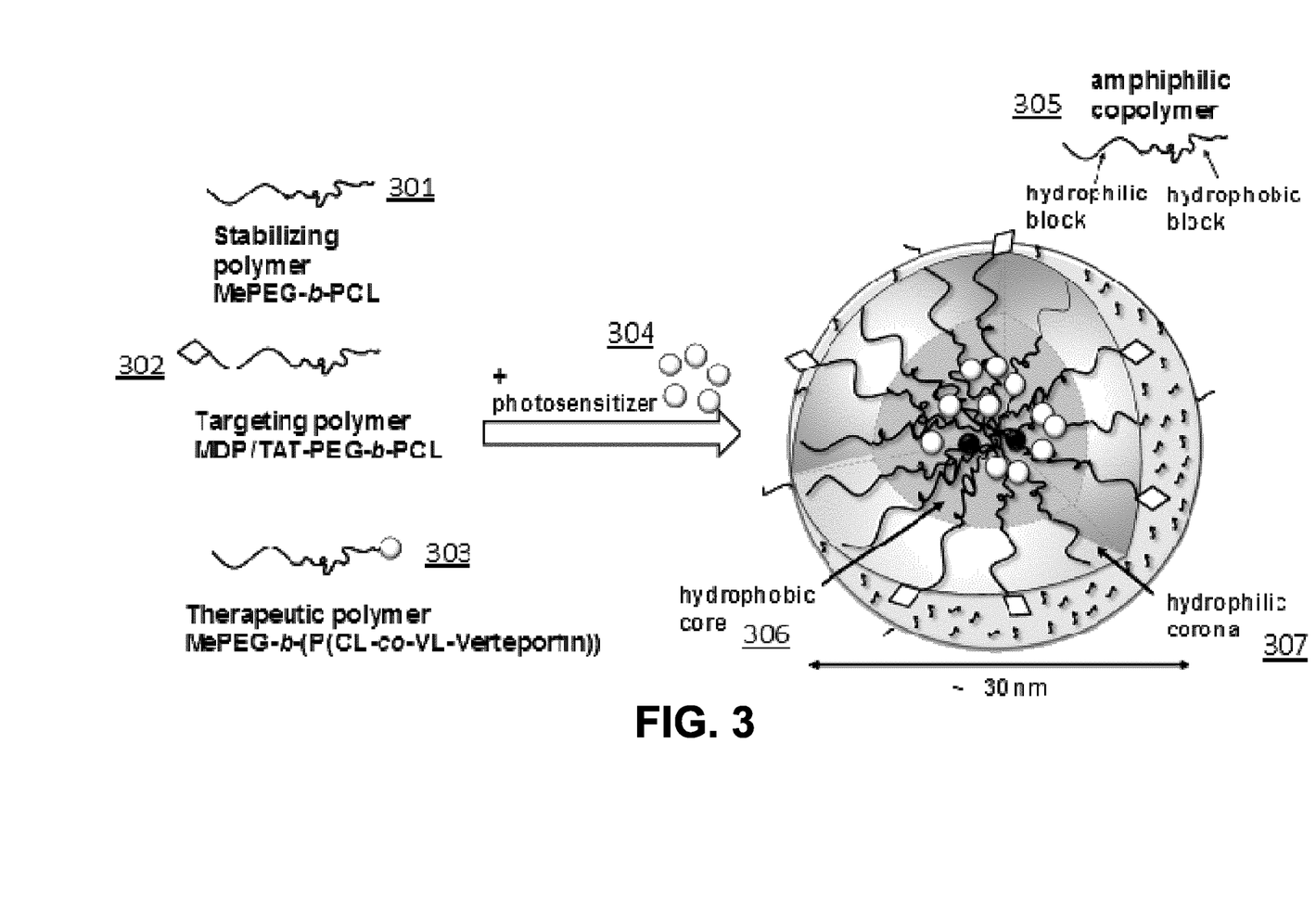
FIG. 3 is a view of an example of a nanoparticle that incorporates a photosensitizer and elements that enhance the delivery of the photosensitizer into the nucleus of target cells such as cancer cells in tumors.

PDT system 102 provides nuclear targeting of photosensitizing material for PDT. For photosensitizing material, mitochondria or other cytoplasmic organelles may be a site of photodynamic damage. However, targeting the photosensitizing material to the cell nucleus may give up to about a 1000-fold reduction in the PDT dose required to achieve the same tumor cell kill. For a given photosensitizing material, this may be equivalent to a corresponding reduction in the required light dose. Other strategies may include the use of nanoparticles and adenoviruses which may have substantial reductions in the required PDT dose. In particular nuclear-targeting dose advantage may be high at low light dose. For example, FIG. 3 shows an example of a nanoparticle that incorporates a photosensitizer and elements that enhance the delivery of the photosensitizer into the nucleus of target cells such as cancer cells in tumors.

PDT system 102 couples to control unit 106 and treatment system 110 (e.g. a treatment planning unit). Treatment system 110 may control clinical treatment and configure treatment parameters such as the doses of ionizing radiation and the resulting CL light source 104 doses. Treatment system 110 may include a processor and memory storing instructions for treatment planning, controlling treatment and configuring the treatment parameters. Control unit 106 connects to PDT system 102 to control treatment parameters during the treatment based on instructions received from treatment system 110. Control unit 106 may actuate and control components of PDT system 102 for treatment. PDT system 102 has nuclear-targeted PDT agent(s) for CL-PDT, where the treatment system 110 enables individually optimized treatment. The treatment system 110 may define a full treatment dose regime which may consider a sensitizer effect to the treatment dose. There may be a dual treatment modality with one excitation beam/source as an example embodiment. The treatment system 110 may define the steepness of the dose for the treatment. Treatment system 110 defines and controls light and PDT dose for the clinical treatment.

According to embodiments described herein, PDT system 102 uses ionizing radiation to generate CL light 104 within the tissue that activates the photosensitizing material located within the nucleus of cells of the target volume. The CL light source 104 may have low intensity. The CL light source 104 may also enable the radiation beam to be imaged and may be used for verification of the treatment delivery to the target. For example, display device 112 may render a visual representation of the images for radiotherapy verification. CL light source 104 may also be used to excite fluorescence, which may be used for imaging of the target or imaging of the photosensitizing material. Direct CL imaging (without an administered fluorescent material) may be used for patient treatment. Accordingly, PDT system 102 may include imaging components for capturing image data for clinical treatment where a visual representation of the image data may be rendered on display device 112 to monitor or verify treatment (via treatment system 110). Display device 112 may couple to PDT system 102 via network 108.

PDT system 102 can deliver photosensitizing material to the nuclei of tissue cells, wherein the photosensitizing agent is targeted to the nucleus of such cells using a nucleus delivery agent. PDT system 102 can activate the photosensitizing material by exposing the tissue cells to CL light source 104 generated by ionizing radiation. The treatment system 110 and control unit 106 can control the ionizing radiation for a dosage level that in the absence of the photosensitizing agent is not therapeutically active. The photosensitizing agent activated by the Cherenkov light damages the nuclear DNA of the tissue cells.

The markedly enhanced PDT efficacy from targeting the photosensitizing material to the cell nucleus, which may be for several different tumor cell lines, may be due to direct DNA damage that gives "biological amplification" through proliferative cell death. This may be compared with the direct cell death by necrosis, apoptosis or autophagy that dominates with extra-nuclear targeting of the photosensitizing material.

Nuclear targeting of photosensitizing material may be used for in vivo tumor PDT in animal models, with impact on tumor growth. NT-PDT and ionizing radiation may be synergistic even at a low radiation dose (6 Gy) that by itself may be substantially sub-therapeutic.

The intensity of CL light source 104 generated in tissue either by external-ray beams or by radionuclides may be low compared with the light levels typically used in PDT using conventional light sources. A practical clinical method may have doses of ionizing radiation that may be substantially sub-therapeutic (as monitored and controlled by treatment system 110 and control unit 106).

PDT system 102 targets the photosensitizing material to the cell nucleus which may provide up to several orders of magnitude reduction in the required PDT light dose (e.g. a treatment parameter of treatment system 110). This may compensate for the low intensity of the CL light source 104 compared to the intensity of conventional PDT light sources.

PDT system 102 generates CL light source 104 in tissues where the PDT is mediated by nuclear-targeted photosensitizing material. This process may be referred to as Cherenkov-activated nuclear-targeted PDT or CHANT-PDT.

In an aspect, embodiments described herein provide generation of the CL light source 104 within the tissue. This may be achieved in various ways. In the first example approach, CL light source 104 can be generated in tissue by an apparatus for ionizing radiation (e.g. as a component of PDT system 102) with use of one or more external beams of high-energy X-rays or high-energy electrons, for example as produced from a linear accelerator (linac). Linacs are used in clinical practice for radiation therapy, operating typically around several MeV energy. More specialized radiation therapy machines such as proton or neutron accelerators may also be used. There is an extensive infrastructure of linacs, radiation dosimetry and radiation treatment planning that will be suitable for CHANT-PDT as components of PDT system 102.

In a second example approach, CL light source 104 may be generated by radioactive materials located on or within the target tissue. This may involve co-injecting a radionuclide together with a photosensitizing agent for CL-activated PDT with nuclear targeting of the photosensitizing material.

In another aspect, embodiments described herein involve targeting the photosensitizing material to the cell nucleus (as a component of PDT system 102). There can be multiple possible mechanisms to achieve this. An example embodiment for nuclear targeting of the photosensitizing material may be to encapsulate the photosensitizing material in polymeric nanoparticles formed from clinically-approved biocompatible materials and conjugated with the TAT peptide for nuclear entry.

Sufficient CL light source 104 may be generated at ionizing radiation doses that are substantially sub-therapeutic, for example about 10 Gy or less, to kill solid tumors through photodynamic activation of photosensitizing material that is localized in the tumor-cell nucleus.

Embodiments described herein may provide devices and processes for the use of CL light source 104 generated by ionizing radiation (as a component of PDT system 102) to activate photosensitizing material located within the nucleus of cells.

Embodiments described herein may provide devices and processes in which the high sensitivity of the cell nucleus to damage from the photoproducts generated within the nucleus compensates for the low radiant energy density of CL light source 104 produced using doses of ionizing radiation that are substantially below the dose required to kill the cells. The doses of ionizing radiation may be controlled by treatment system 110.

Figure 2:
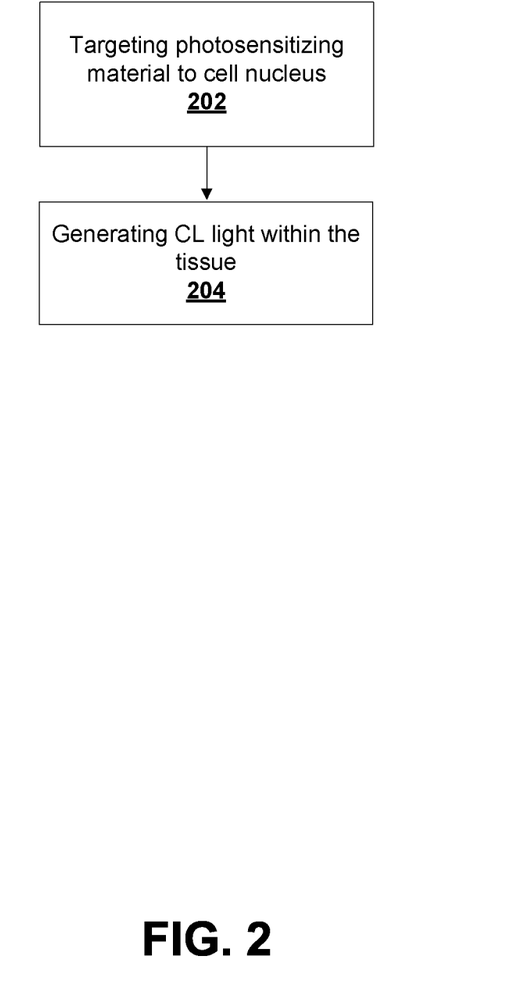
FIG. 2 is a view of an example process for photodynamic therapy according to some embodiments.

FIG. 2 is a view of an example process for photodynamic therapy configured to generate Cherenkov light by ionizing radiation to activate photosensitizing material located within the nucleus of cells.

At 202, PDT system 102 targets photosensitizing material to the nucleus of cells with doses controlled by treatment system 110. PDT system 102 can deliver photosensitizing material to the nuclei of tissue cells and the photosensitizing agent can targeted to the nucleus of such cells using a nucleus delivery agent.

At 204, PDT system 102 generates CL light source 104 within the tissue. Alternatively, the CL light source 104 may be generated in dielectric material in close proximity to the tissue.

The PDT system 102 can trigger activation of the photosensitizing material by exposing the tissue cells to CL light source 104 generated by ionizing radiation. The treatment system 110 and control unit 106 can control the ionizing radiation at a dosage level that in the absence of the photosensitizing agent is not therapeutically active. The photosensitizing agent activated by the CL light source 104 damages the nuclear DNA of the tissue cells.

As noted, generating CL light source 104 within the tissue may be achieved in various ways. For example, CL light source 104 can be generated in tissue by ionizing radiation by the use of one or more external beams of high-energy X-rays or high-energy electrons produced from linacs or specialized radiation therapy machines such as proton or neutron accelerators. The radiation dose may be controlled by treatment system 110. As another example, the CL light source 104 may be generated by radioactive materials located on or within the target tissue. This may involve co-injecting a radionuclide together with the photosensitizing material.

Embodiments described herein may provide devices and processes in which the CL light source 104 is generated within tissue. Embodiments described herein may provide devices and processes in which the CL light source 104 is generated in dielectric material in close proximity to the tissue.

Embodiments described herein may provide devices and processes in which the cells of the target volume are tumor cells or other diseased cells. Embodiments described herein may provide devices and processes in which the cells are killed or modified by the photoproducts generated by the activation of the photosensitizing material by the CL light source 104.

In an aspect, embodiments described herein provide nuclear-targeted PDT agent(s) specifically for CHANT-PDT. The PDT agents become active though the CL generated by low-dose ionizing radiation.

In some example embodiments, the PDT dose may be painted to the affected area or target volume.

An aspect of the devices, systems and processes described herein may be implemented in a combination of both hardware and software. Aspects of the embodiments may be implemented on programmable computers, each computer including at least one processor, a data storage system (including volatile memory or non-volatile memory or other data storage elements or a combination thereof), and at least one communication interface.

Program code is applied to input data to perform the functions described herein and to generate output information. The output information is applied to one or more output devices. In some embodiments, a communication interface may connect hardware components. In embodiments in which elements may be combined, the communication interface may be a software communication interface, such as those for inter-process communication. In still other embodiments, there may be a combination of communication interfaces implemented as hardware, software, and combination thereof.

The discussion provides many example embodiments. Although each embodiment represents a single combination of inventive elements, other examples may include all possible combinations of the disclosed elements. Thus if one embodiment comprises elements A, B, and C, and a second embodiment comprises elements B and D, other remaining combinations of A, B, C, or D, may also be used.

The term "connected" or "coupled to" may include both direct coupling (in which two elements that are coupled to each other contact each other) and indirect coupling (in which at least one additional element is located between the two elements).

An aspect of embodiments may be in the form of a software product for treatment system 110 or a treatment planning software product. The software product may be stored in a non-volatile or non-transitory storage medium, which can be a compact disk read-only memory (CD-ROM), a USB flash disk, or a removable hard disk. The software product includes a number of instructions that enable a computer device (personal computer, server, or network device) to execute the methods provided by the embodiments.

An aspect of embodiments may be implemented by physical computer hardware, including computing devices, servers, receivers, transmitters, processors, memory, displays, and networks. The embodiments described herein provide useful physical machines and particularly configured computer hardware arrangements.

Although the embodiments have been described in detail, it should be understood that various changes, substitutions and alterations can be made herein without departing from the scope as defined by the appended claims.

Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed, that perform substantially the same function or achieve substantially the same result as the corresponding embodiments described herein may be utilized. Accordingly, the appended claims are intended to include within their scope such processes, machines, manufacture, compositions of matter, means, methods, or steps.

Embodiments described herein relate to targeting the photosensitizer to the nuclei of cells in the target tissues. This may enable low light levels such as the CL light source 104 generated by X-rays to be sufficient to activate the photosensitizer to produce the required biological response and subsequent clinical outcome.

FIG. 3 shows an example embodiment to achieve nuclear targeting. As shown, there may be a stabilizing component 301 combined with a targeting component 302 combined with a therapeutic component 303. An illustrative example combination is MePEG-b-(P(CL-co-VL-Verteporfin)) where the photosensitizer verteporfin 304 is entrapped within nanoparticles that are typically about 10 to about 100 nm in diameter formed from amphiphilic block copolymers 305. These nanoparticles have a hydrophobic core 306 and a hydrophilic corona or shell 307 that enable incorporation of the photosensitizer as well as suitable pharmacologic properties for in vivo administration. These nanoparticles then target the cell nucleus through for example attachment of TAT (Trans-Activator of Transcription) peptide. Other photosensitizers with suitable chemical and photophysical properties may be used.

In an aspect Cherenkov-activated nuclear-targeted PDT can be achieved according to the following process. First, the agent used to achieve nuclear targeting of a photosensitizer is synthesized and characterized. Second, it is demonstrated that such nuclear targeting results in increased DNA damage compared to the same photosensitizer without nuclear targeting.

The particular example of nuclear targeting of photosensitizer utilizes conjugates of block copolymer micelles (BCM) and photosensitizer tetraphenyl porphyrin (TPP) that is then formed into nanoparticles (NPs) that include a nuclear localizing signal (NLS) in the form of a particular peptide sequence.

Figure 4:
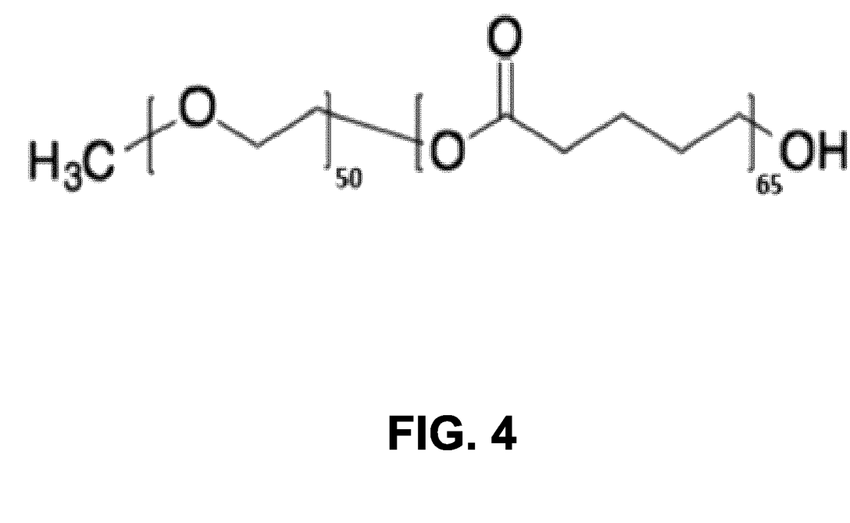
FIG. 4 shows the molecular structure of a block copolymer micelle according to an aspect of the present invention.

Polyester copolymers metoxy-polyethylene glycol-block-polyvalerolactone (mPEG-b-PVL) can be prepared. An example molecular structure of this is shown in FIG. 4.

Figure 5:
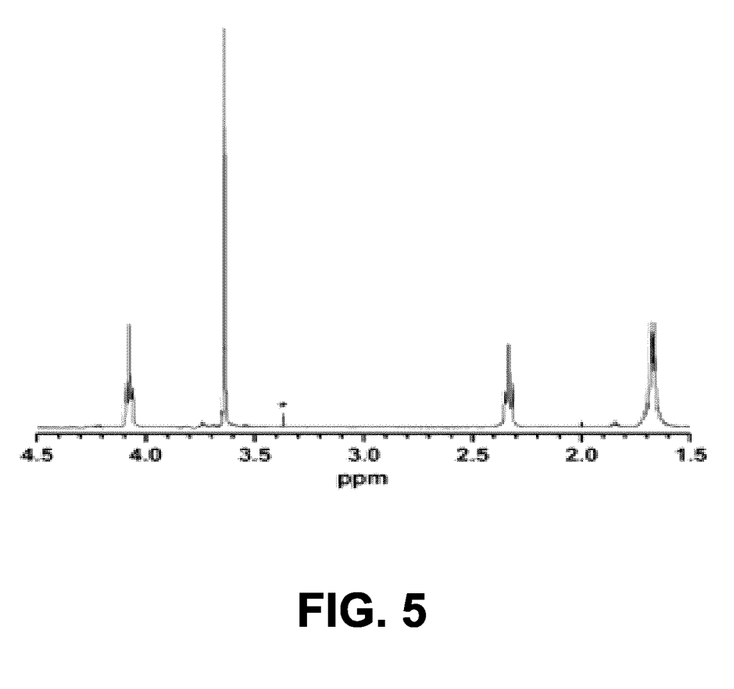
FIG. 5 shows the $^1$H nuclear magnetic resonance (NMR) spectrum of an mPEG-b-PVL according to an aspect of the present invention.

In an example, the synthesis was as follows. In a flame-dried round two-neck flask, the 2 mol % of the catalyst 1,5,7-triazabicyclo[4.4.0]dec-5-ene (TBD) was added and dried under vacuum. Anhydrous toluene and 2 kiloDalton mPEG (mPEG2k) were then combined in the flask with TBD under argon and stirred for 30 minutes. Distilled monomer was transferred by cannulation in the reaction vessel under positive pressure of argon. Polymerization was carried out at room temperature for 6 hours. The slurry solution was first precipitated in cold methanol, re-dissolved in tetrahydrofurane (THF) and then precipitated in of a mixture of hexane/ethyl ether (30/70 v/v). Yield was >90% (w/w). The $^1$H nuclear magnetic resonance (NMR) spectrum of the mPEG-b-PVL was recorded on a Bruker AMX400 spectrometer. This is shown in FIG. 5.

The molecular weight was determined by gel permeation chromatography (GPC) analysis in THF using a Waters 2695 system that includes two PLgel 5 μm Agilent columns and a Waters 2414 RI detector. A calibration curve was constructed using polystyrene standards. Dynamic light scattering (DLS) measurements were carried out on a Q100 TA thermal analysis system over different temperature ranges with a common heating rate of 10° C./min under nitrogen (3 cycles).

The copolymer aggregates (BCMs) and the BCM-TPP conjugate were prepared using a solvent evaporation method. Briefly, 20 mg of copolymer and 5 mg of TPP was dissolved in 2 mL of THF. After stirring in the dark for 15 min, the copolymer and TPP solutions were added drop wise to 20 mL of distilled water with stirring. After 48 hours under stirring in the dark, the copolymeric solutions were centrifuged (5000 rpm for 10 min) and the supernatant was purified by ultrafiltration (100 KDa) (3 volumes). The encapsulation efficiency (EE) and drug loading (DL) of TPP in BCMs was quantified by fluorescence spectroscopy. Briefly, an aliquot of the formulation (10 μL) was diluted in 9 mL dissolution media (1:1) [(10% (v/v) triton X-100): (0.75N HCl Isopropanol)] and then quantified fluorometrically (440 excitation, 685 nm detection). TPP release was performed in PBS pH 7.4 in the absence or the presence of bovine serum albumin (BSA 50 mg/mL) under sink conditions. An aliquot (2 mL) of the external media (PBS pH 7.4+Tween 80 0.5% w/v) was removed at a predetermined time and replaced with fresh buffer. Samples were kept at −20° C. until analysis by spectrofluorometry as described above.

Figure 6:
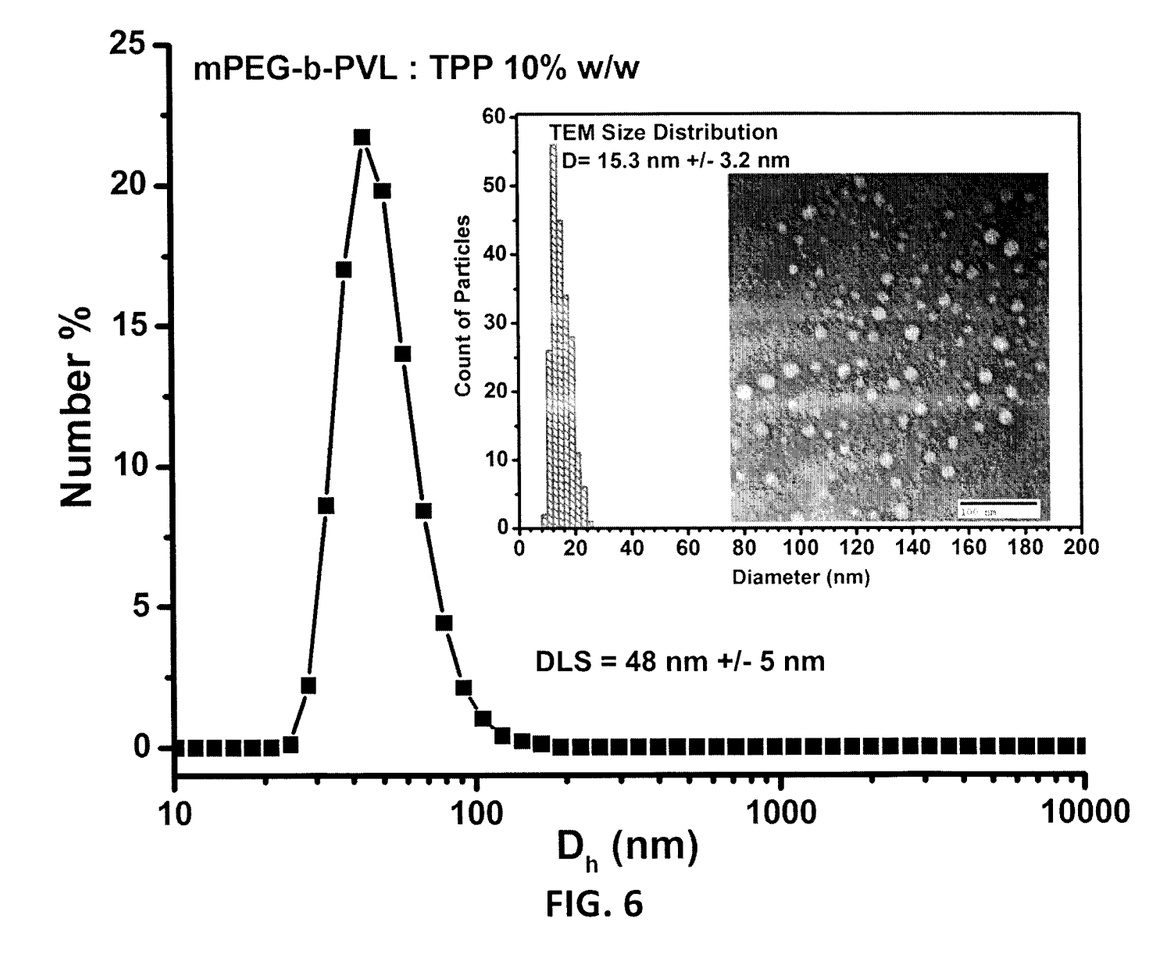
FIG. 6 shows dynamic light scattering and transmission electron microscope measurements of copolymer aggregates according to an aspect of the present invention.

Dynamic light scattering (DLS) of aqueous samples was performed with a Malvern DLS-Zetasizer Nano ZS instrument equipped with a 4 mW, 633 nm He—Ne laser. Measurements were conducted in backscattering (173°) mode and detected with an avalanche photodiode. Experiments were repeated seven times at 25° C. The correlation functions were analyzed by a non-negative least-squares (NNLS) algorithm. The morphology of the BCMs before and after TPP loading was observed by transmission electron microscopy (TEM) by gently dispersing 5-10 μL of a copolymer solution onto a 200-mesh copper grid coated with carbon film. Excess solution was removed carefully using paper, left to air dry and the sample was then negatively stained using a uranyl acetate (UA) solution (1%, w/v) for 20 seconds. The excess UA was subsequently removed using paper. The negative stain surrounds the material with an electron dense layer generating reverse contrast, negative electron images. The DLS and TEM measurements are shown in FIG. 6.

Figure 7:
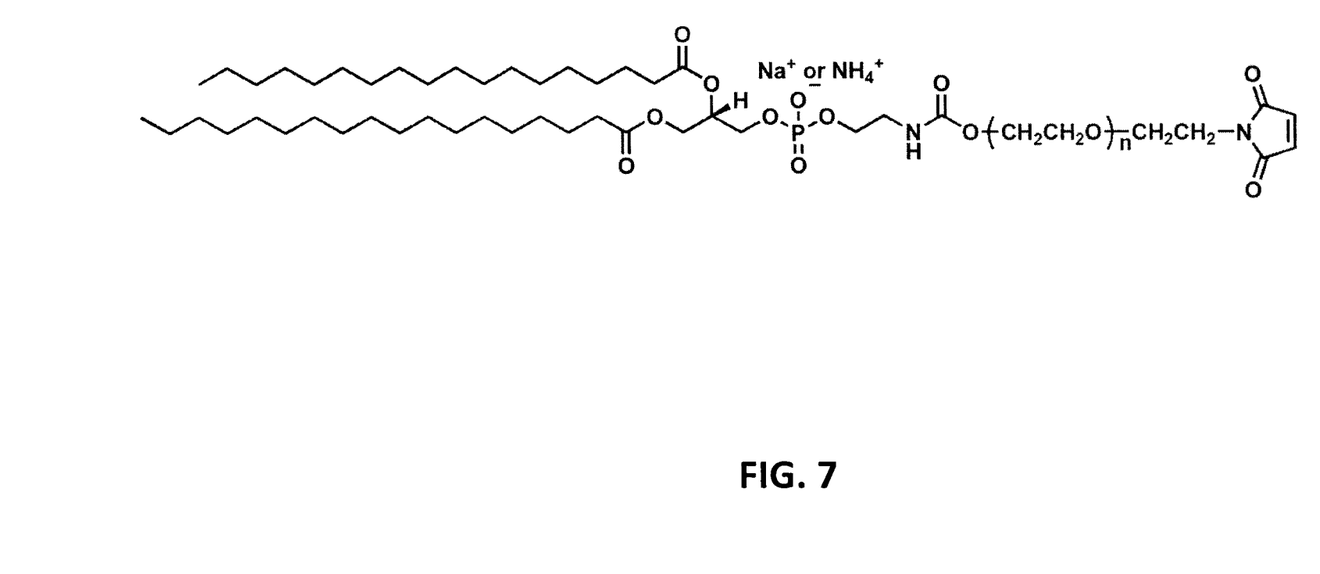
FIG. 7 shows the structure of a block-copolymer-photosensitizer conjugate according to an aspect of the present invention.

In order to incorporate the NLS 35 mg of DSPE-PEG5K-Maleimide and 12 mg of NLS-SH peptide (BioBasic Canada$^{inc}$, sequence HS-CGYGPKKKRKVGG—molecular weight=1419.72 g·mol$^{-1}$) were dispersed in 1 mL of PBS at pH 7.4 containing 4 mM EDTA, dissolved using sonication and purged with argon. After 24 hours of reaction under stirring, 2 mL of distilled water was added prior to extensive dialysis for 48 hours. The reaction mixture was then frozen at −80° C. prior to freeze drying. The yield was >90% (w/w). MALDI-TOF mass spectrometry (MS) was performed to confirm the conjugation on a Bruker Autoflex instrument, with 20 kV extraction voltage and a $N_2$ laser at 337 nm. α-cyano-4-hydroxycinnamic acid was used as the matrix with added lithium chloride (LiCl) for the analysis. 1,2-distearoyl-sn-glycero-3-phosphoethanolamine-PEG-maleimide (DSPE-PEG5K-mal) and samples (conjugate+matrix+LiCl) were applied to the target plate by the dried-droplet method. FIG. 7 shows the structure of the conjugate, with the photosensitizer at the right end of the copolymer.

Following preparation of the nuclear-targeted copolymer-photosensitizer micelles (NPs) as above, tests were carried out of the effect on pancreatic cancer cells in tissue culture (in vitro) of X-ray irradiation under conditions that generate Cherenkov light. Pancreatic cells (BxPC-3: ATCC, VA, USA) were selected since treatment of pancreatic cancer is one example of how the current invention might be applied to address an unmet clinical need for a minimally invasive therapy for this highly fatal disease where conventional treatments such as radiation or chemotherapy are inadequate.

Cells were incubated with NPs with water as the vehicle. Alternatively, cells were incubated with TPP only at the same concentration in water (4 micrograms per ml in the medium) and for the same incubation time (6 h) as a control. A further control was to add only the vehicle (water) to the medium in the same volume as for the NPs or TPP. After incubation the cells were washed 3 times with Hank's balanced salt solution (HBSS).

The chambered slides containing the cells were then placed in 10 cm diameter dishes that were covered with plastic film to create a water-tight enclosure. The dishes were then placed at the center of a 20 cm×20 cm×15 cm polystyrene tank containing water that served as material for Cherenkov generation, simulating a typical clinical set up. The tank was then exposed to an X-ray beam from a clinical 18 MV linac to a dose of 10 Gy. The time from the final wash to the end of X-ray exposure was approximately 45 minutes.

Figure 8:
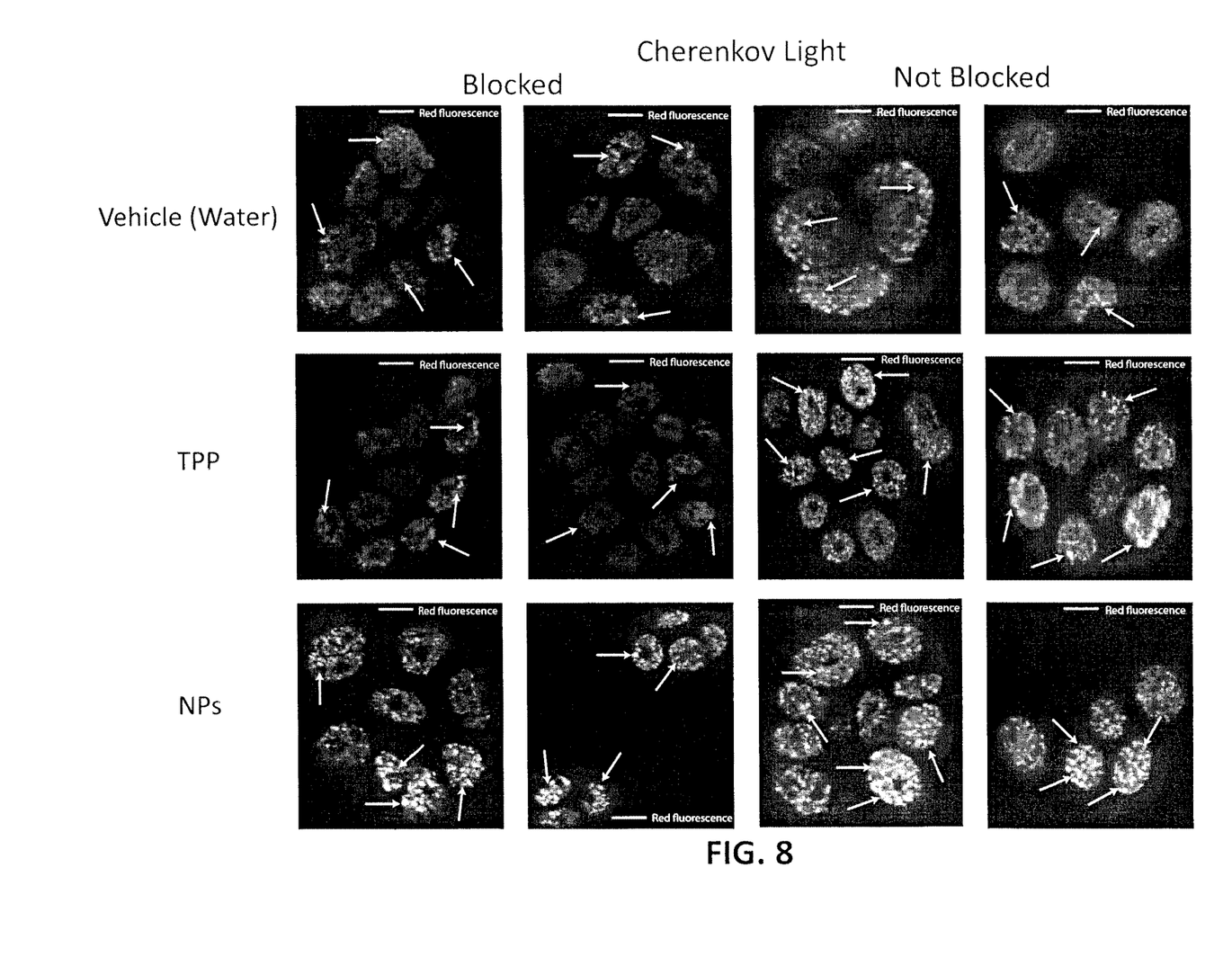
FIG. 8 shows fluorescence images of cells treated with CHANT-PDT according to an aspect of the present invention.

At 30 minutes after irradiation, the damage to DNA in the cells was measured using phospho-gamma H2AX immunofluorescence assay, similar to that used for example by Fraser et al. (2012). This used a primary antibody (anti-phospho-gamma H2A.X (Ser 139), clone JBW301, mouse monoclonal: EMD Millipore, Billerica, Mass., USA) and secondary antibody (goat anti-mouse IgG (H+L) cross-absorbed secondary antibody, AF488: Life Technologies, CA, USA). This shows double-strand breaks as red fluorescence within the cell nucleus. The cells were also stained with 4',6-diamidino-2-phenylindole (DAPI: Life Technologies, CA, USA) to highlight the nuclei. The fluorescence was imaged on a confocal fluorescence microscope where the red fluorescence (488+/−10 nm excitation, >505 nm detection) corresponding to DNA double strand breaks could be visualized on the green DAPI fluorescence background (405+/−10 nm excitation, 460+/−25 nm detection) and the intensity quantified. The red fluorescence intensity counts were integrated over 10-18 cells for each treatment condition. FIG. 8 shows examples of the fluorescence images.

A control was performed, exposing the cells without prior incubation in either NPs or TPP, that is with only water added, in order to measure the DNA damage caused directly by exposure to the X-rays and Cherenkov light. A further control was to block the Cherenkov light generated in the surrounding water volume from reaching the cells by wrapping the dishes containing the cell plates in blackout material. This did not eliminate the Cherenkov light generated within the dishes, culture medium, plates or cell themselves.

Figure 9:
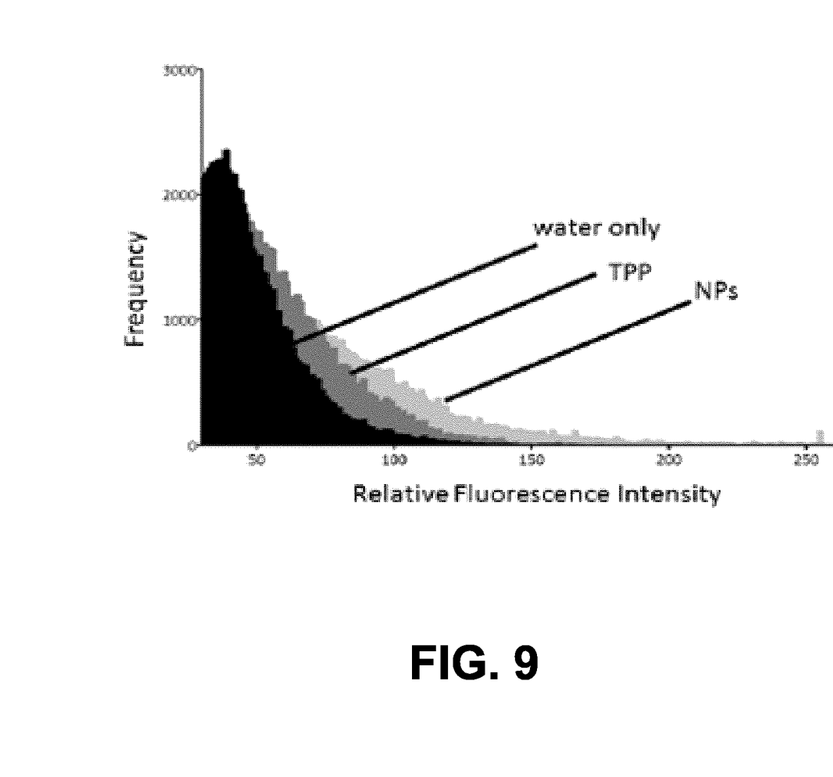
FIG. 9 shows frequency distributions of fluorescence intensity in cells treated with CHANT-PDT according to an aspect of the present invention.
Figure 10:
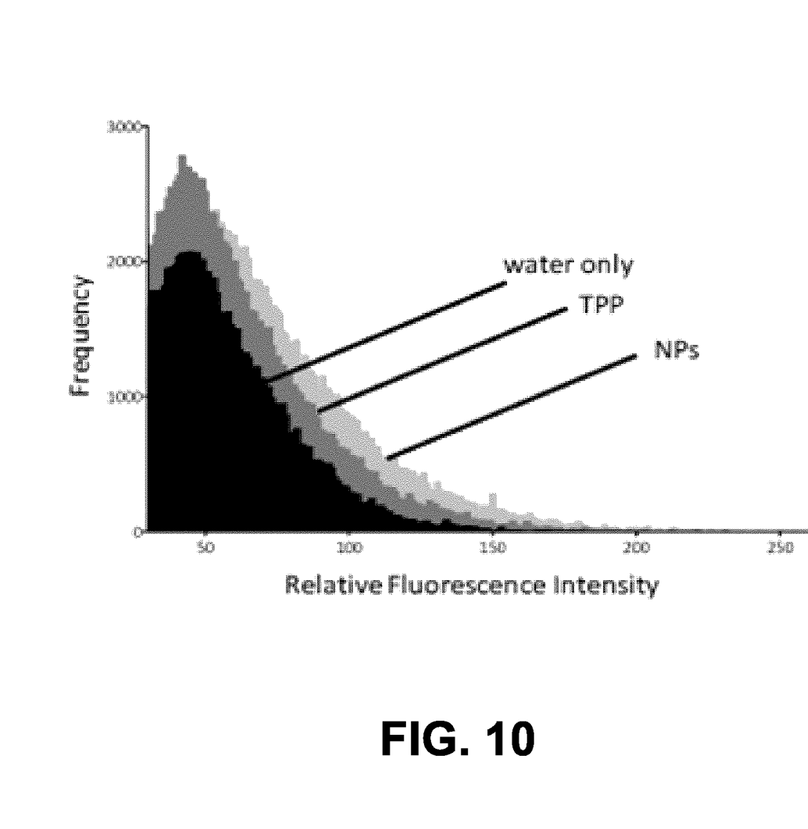
FIG. 10 shows frequency distributions of fluorescence intensity in a control sample of cells not exposed to Cherenkov light.

Examples of the frequency distributions of the fluorescence intensity are shown in FIG. 9 for the case of exposure to the CL light source 104 and in FIG. 10 when the CL light source 104 was blocked from reaching the cells. In each case the distributions are shown for X-ray only (water only added to the incubation medium), NPs added to the medium and TPP added to the medium.

The total and mean fluorescence intensity counts for each experiment (+/−1 standard deviation) are summarized in Table 1.

TABLE 1

| Incubation material | Cherenkov | Mean fluorescence intensity counts |
|---|---|---|
| NPs | unblocked | 72.0 +/− 4.5 |
| NPs | blocked | 60.0 +/− 6.3 |
| TPP | unblocked | 49.5 +/− 6.7 |
| TPP | blocked | 54.8 +/− 6.0 |
| water | unblocked | 44.3 +/− 4.5 |
| water | blocked | 51.9 +/− 4.5 |

These data were tested for statistical significance. The relative mean fluorescence intensities were significantly different between: a) incubation in NPs with exposure to Cherenkov light versus incubation in TPP with exposure to Cherenkov light (p=0.0064) and b) incubation in NPs with exposure to Cherenkov versus incubation in water with exposure to Cherenkov (p=0.0017). No other paired comparisons were statistically significant (p>0.05).

These exemplary non-limiting experiments can demonstrate that, among other things, photosensitizer can be incorporated into copolymer nanoparticles that also carry a nuclear localizing signal in the form of a peptide sequence, that cancer cells can take up this material upon incubation, that at least part of this material can be taken up into the cell nucleus, and that subsequent exposure to Cherenkov light generated within a tissue-simulating material containing the cells leads to increased number of double strand breaks in the nuclear DNA compared to the same incubation with the photosensitizer without nuclear targeting and compared with the double strand breaks due to the X-rays alone.

As can be understood, the examples described above and illustrated are intended to be exemplary only.

What is claimed is:

1. A method of photodynamic therapy comprising:
   delivering photosensitizing material to a nucleus of tissue cells, wherein the photosensitizing material is targeted to the nucleus of the tissue cells using a nucleus delivery agent;
   activating the photosensitizing material by exposing the photosensitizing material to secondary products of ionizing radiation generated when the ionizing radiation is directed at tissue, wherein the secondary products of ionizing radiation comprise Cherenkov light; and causing DNA damage in the tissue cells by photoproducts generated by activation of the photosensitizing material.

2. The method of claim 1, wherein the photosensitizing material is a porphyrin.

3. The method of claim 2, wherein the porphyrin is tetraphenylporphyrin.

4. The method of claim 1, wherein the nucleus delivery agent comprises a nuclear localizing signal attached to at least one of:
the photosensitizing material; or
a nanosized carrier that incorporates the photosensitizing material.

5. The method of claim 4, wherein the nanosized carrier is at least one of:
formed from polymers, lipids or small-molecule surfactants; or
a block-copolymer micelle.

6. The method of claim 1, wherein the ionizing radiation is at a dosage level that is therapeutically effective with use of the photosensitizing material.

7. The method of claim 1, wherein the DNA damage in the tissue cells caused by activation of the photosensitizing material is in addition to any DNA damage caused by the ionizing radiation alone.

8. The method of claim 1, further comprising delivering the ionizing radiation at a dosage level less than 10 Gy.

9. The system of claim 1, wherein the photosensitizing material is activated based on treatment parameters comprising doses of the ionizing radiation and doses of the Cherenkov light.

10. A non-transitory computer readable-medium storing instructions for photodynamic therapy treatment planning, the instructions, when executed by a computing device, cause the device to:
configure treatment parameters to activate photosensitizing material delivered to nuclei of tissue cells by exposing the photosensitizing material to secondary products of ionizing radiation generated when the ionizing radiation is directed at tissue, wherein the secondary products of the ionizing radiation comprise Cherenkov light, wherein the treatment parameters comprise doses of the ionizing radiation and doses of the Cherenkov light, wherein the photosensitizing material is targeted to the nuclei of the tissue cells using a nucleus delivery agent; and
wherein DNA damage is caused in the tissue cells by photoproducts generated by activation of the photosensitizing material by exposing the tissue cells to the Cherenkov light.

11. The non-transitory computer readable-medium of claim 10, wherein the photosensitizing material is a porphyrin.

12. The non-transitory computer readable-medium of claim 11, wherein the porphyrin is tetraphenylporphyrin.

13. The non-transitory computer readable-medium of claim 10, wherein the nucleus delivery agent comprises a nuclear localizing signal attached to at least one of:
the photosensitizing material; or
a nanosized carrier that incorporates the photosensitizing material.

14. The non-transitory computer readable-medium of claim 13, wherein the nanosized carrier is at least one of:
formed from polymers, lipids or small-molecule surfactants; or
a block-copolymer micelle.

15. The non-transitory computer readable-medium of claim 10, wherein the ionizing radiation is at a dosage level that is therapeutically effective with use of the photosensitizing material.

16. A method of photodynamic therapy comprising:
delivering photosensitizing material to nuclei of tissue cells, wherein the photosensitizing material is targeted to the nuclei of said cells using a nucleus delivery agent; and
activating the photosensitizing material by exposing the tissue cells to Cherenkov light generated by ionizing radiation, the ionizing radiation at a dosage level that is therapeutically effective with use of the photosensitizing material.

17. The method of claim 16, wherein the photosensitizing material activated by the Cherenkov light damages nuclear DNA of the tissue cells.

18. A system for photodynamic therapy, the system comprising:
a nucleus delivery agent to deliver photosensitizing material to nuclei of tissue cells, wherein the photosensitizing material is targeted to each nucleus of said nuclei of said cells using the nucleus delivery agent; and
a hardware processor to control delivery of ionizing radiation to activate the photosensitizing material by exposing the tissue cells to Cherenkov light generated by the ionizing radiation, the ionizing radiation is at a dosage level that is therapeutically effective with use of the photosensitizing material.

19. The device of claim 18, wherein the photosensitizing material activated by the Cherenkov light damages nuclear DNA of the tissue cells.

20. The system of claim 18, wherein the dosage level of the ionizing radiation is less than 10 Gy.

21. The system of claim 18, wherein the dosage level of the ionizing radiation is based on treatment parameters comprising doses of the ionizing radiation and doses of the Cherenkov light.

22. A system for photodynamic therapy (PDT), the system comprising:
a nucleus delivery agent to deliver photosensitizing material to nuclei of tissue cells, wherein the photosensitizing material is targeted to the nuclei of said cells using the nucleus delivery agent;
an apparatus for ionizing radiation to activate the photosensitizing material by exposing the tissue cells to Cherenkov light generated by the ionizing radiation; and
a control unit to control, based on treatment parameters, delivery of the ionizing radiation at a dosage level that is therapeutically effective with use of the photosensitizing material, wherein the treatment parameters comprise doses of the ionizing radiation and doses of the Cherenkov light.

* * * * *